(12) United States Patent
Deamer

(10) Patent No.: US 6,617,113 B2
(45) Date of Patent: Sep. 9, 2003

(54) METHODS OF DETERMINING THE PRESENCE OF DOUBLE STRANDED NUCLEIC ACIDS IN A SAMPLE

(75) Inventor: David W. Deamer, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/151,630

(22) Filed: May 16, 2002

(65) Prior Publication Data

US 2002/0137089 A1 Sep. 26, 2002

Related U.S. Application Data

(63) Continuation of application No. 09/656,302, filed on Sep. 6, 2000, now Pat. No. 6,428,959.
(60) Provisional application No. 60/152,673, filed on Sep. 7, 1999.

(51) Int. Cl.$^7$ .................................................. C12Q 1/68
(52) U.S. Cl. ............................. 435/6; 435/4; 435/285.2; 435/287.2; 435/287.3; 436/2; 436/151
(58) Field of Search ............................. 435/4, 6, 285.2, 435/287.3, 287.2; 436/2, 151

(56) References Cited

U.S. PATENT DOCUMENTS

| | | | |
|---|---|---|---|
| 5,795,782 A | 8/1998 | Church et al. | ................. 435/6 |
| 6,428,959 B1 * | 8/2002 | Deamer | ......................... 435/6 |

OTHER PUBLICATIONS

Akeson et al. "Microsecond time–scale discrimination among polycytidylic acid, polyadenylic acid, and polyuridylic acid as homopolymers or as segments within single RNA molecules," *Biophysical Journal*, vol. 77, No. 6, Dec. 1999.
Deamer et al. "Nanopores and nucleic acids; prospects for ultrarapid sequencing," *Trends in Biotechnology*, vol. 18, No. 4, Apr. 2000.
Deamer et al. "Characterization of nucleic acids by nanopore analysis," *Accounts of Chemical Research*, vol. 35, No. 10, Oct. 2002.
Montal et al. "Formation of Bimolecular membranes from lipid mono layers and a study of their electrical properties," *Proceedings of the National Academy of Sciences of the United States*, vol. 69, No. 12, 1972.
Szabo et al. "Double–stranded DNA can be translocated across a planar membrane containing purified mitochondrial porin," *FASEB Journal*, vol. 12, No. 6, pp. 496–497, 500. Apr. 1998.
Bezrukov et al. "Counting polymers moving through a single ion channel," *Nature*, vol. 370, pp. 230–231, Jul. 1994.
C.P. Bean,et al. "Etching of Submicron Pores in Irradiated Mica", *Journal of Applied Physics*, vol. 41, No. 4, Mar. 15, 1970.
Ralph W. Deblois, et al. "Electrokinetic Measurements with Submicron Particles and Pores by the Resistive Pulse Technique", *Journal of Colloid and Interface Science*, vol. 61, No. 2, Sep. 1977.
John J. Kasianowicz, et al., "Characterization of Individual Polynucleotide Molecules Using A Membrane Channel", *Proc. Natl. Acad. Sci. USA*, vol. 93, pp. 13770–13773, Nov. 1996.

* cited by examiner

Primary Examiner—Carla J. Myers
(74) Attorney, Agent, or Firm—Brett E. Field; Bozicevic, Field & Francis

(57) ABSTRACT

Methods for determining the presence of double stranded nucleic acids in a sample are provided. In the subject methods, nucleic acids present in a fluid sample are translocated through a nanopore, e.g. by application of an electric field to the fluid sample. The current amplitude through the nanopore is monitored during the translocation process and changes in the amplitude are related to the passage of single- or double-stranded molecules through the nanopore. The subject methods find use in a variety of applications in which the detection of the presence of double-stranded nucleic acids in a sample is desired, e.g. in hybridization assays, such as Northern blot assays, Southern blot assays, array based hybridization assays, etc.

14 Claims, 1 Drawing Sheet

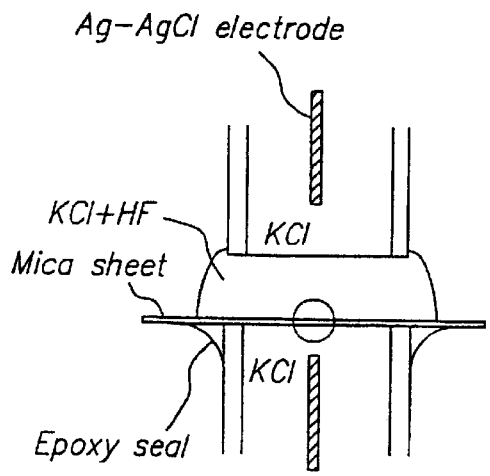
FIG. 1A
FIG. 1B
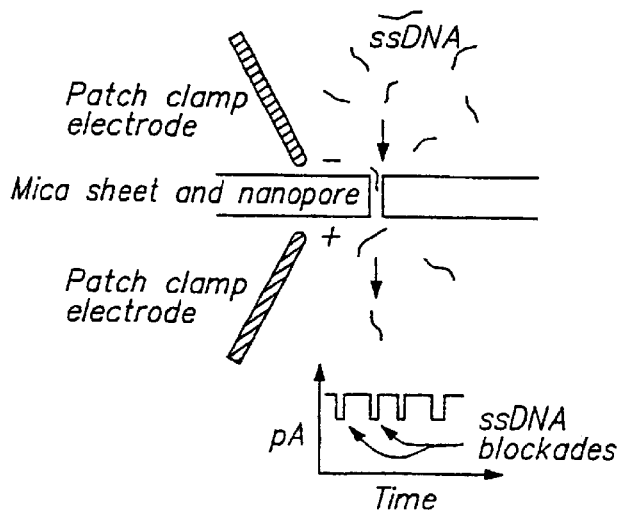
FIG. 2A
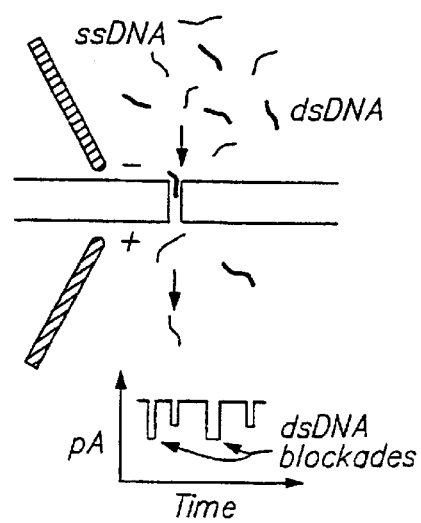
FIG. 2B

METHODS OF DETERMINING THE PRESENCE OF DOUBLE STRANDED NUCLEIC ACIDS IN A SAMPLE

CROSS REFERENCE TO RELATED APPLICATIONS

Pursuant to 35 U.S.C. §119(e), this application is a continuation of U.S. patent application Ser. No. 09/656,302, filed Sep. 6, 2000, now U.S. Pat. No. 6,428,959 which claims benefit of United States Provisional Patent Application Serial No. 60/152,673 filed Sep. 7, 1999, the disclosure of which is herein incorporated by reference.

ACKNOWLEDGMENT

This invention was made with United States Government support under Grant Nos. NIH RO1 HG/OD01360-01 and HG 01826-01B awarded by the NIH. The United States Government has certain rights in this invention.

INTRODUCTION

1. Field of the Invention

The field of this invention is nucleic acid hybridization.

2. Background of the Invention

The detection of nucleic acid hybridization events is a fundamental measurement in a variety of different life science research, diagnostic, forensic and related applications. A common feature of nucleic acid hybridization assays is that target and probe nucleic acids are combined under hybridization conditions and any hybridization events occurring between complementary target and probe nucleic acids are detected. The detection of hybridization events, i.e. target/probe duplexes, is then used to derive information about the source of the target nucleic acids, e.g. the genes expressed in a cell or tissue type, and the like.

In currently employed hybridization assays, the target nucleic acid must be labeled with a detectable label (where the label may be either directly or indirectly detectable), such that the presence of probe/target duplexes can be detected following hybridization. Currently employed labels include isotopic and fluorescent labels, where fluorescent labels are gaining in popularity as the label of choice, particularly for array based hybridization assays.

While fluorescent labels provide a number of advantages over other types of labels in hybridization assays, they are not ideal. For example, it is difficult to obtain quantitative results with fluorescent labels. Furthermore, fluorescent label based assays can be relatively slow and are difficult to scale up.

Accordingly, there is continued interest in the development of new hybridization assay protocols. Of particular interest would be the development of a hybridization assay protocol in which the presence of hybridized target and probe could be detected without the use of labels, such as fluorescent labels.

Relevant Literature

Bean et al., J. Appl. Phys. (1970) 41:1454–1459; DeBlois et al., J. Coll. Interface (1977) 61:323–335; and Kasianowicz et al., Proc. Nat'l Acad. Sci. USA (1996) 93:13770–13773.

SUMMARY OF THE INVENTION

Methods are provided for determining the presence of double stranded nucleic acids in a sample. In the subject methods, nucleic acids present in a fluid sample are translocated through a nanopore, e.g. by application of an electric field to the fluid sample. The current amplitude through the nanopore is monitored during the translocation process and changes in the amplitude are related to the passage of single- or double-stranded molecules through the nanopore. The subject methods find use in a variety of applications in which detection of the presence of double-stranded nucleic acids in a sample is desired, e.g. in hybridization assays, such as Northern blot assays, Southern blot assays, array based hybridization assays, etc.

BRIEF DESCRIPTION OF THE FIGURES

FIGS. 1A & B provide a representation of the preparation of a mica nanopore device that may be used to practice the methods of the subject invention.

FIGS. 2A and 2B provide representations of the subject methods.

DESCRIPTION OF THE SPECIFIC EMBODIMENTS

Methods for determining the presence or absence of double stranded or hybridized nucleic acids in a fluid sample are provided. In the subject methods, a sample suspected of having double stranded nucleic acids is contacted with a nanopore and nucleic acids present in the sample are sequentially translocated through the nanopore, e.g. by application of an electric field to the fluid sample and across the nanopore. The current amplitude through the nanopore is monitored during the translocation step. The presence of double stranded nucleic acids present in the sample is then determined from the measured current amplitude values. The subject methods find use in a variety of applications and are particularly useful for monitoring hybridization events in hybridization based assays, e.g. Northern blots, Southern blots, array based hybridization assays, etc.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

As summarized above, the subject invention provides methods for determining the presence of double stranded nucleic acids in a fluid sample. By nucleic acid is meant a polymer composed of nucleotides, e.g. deoxyribonucleotides or ribonucleotides. As such, nucleic acids include "ribonucleic acid" or "RNA" and "deoxyribonucleic acid" or "DNA." In many embodiments, the nucleic acids of interest are DNA molecules. The length of the nucleic acids which may be characterized as single or double stranded by the subject methods generally ranges from at least about 5 nt, usually at least about 10 nt and more usually at least about 100 nt to lengths of up to 1000 nt or longer. As such, nucleic acids that may be characterized according to the subject invention include oligonucleotides and polynucleotides, including in some embodiments long polynucleotides, e.g. cDNAs, etc.

The nucleic acids that may be characterized by the subject methods are present in a fluid sample, specifically a liquid sample. The sample must be an electrically conductive sample, i.e. the nucleic acids must be dissolved in an electrically conductive solvent. Any convenient electrically conductive solvent may be employed. In many embodiments, the solvent is an aqueous solvent, where the solvent may be pure water or water in which one or more additional agents are present, e.g. buffering agents, salts (e.g. potassium chloride), and the like. The pH of the fluid sample typically ranges from about 6.0 to 9.0, and more usually from about 7.0 to 8.5. The source of the sample will vary greatly depending on the particular application in which the subject methods are employed, where representative applications are described in greater detail below. For example, the sample may be a spot of fluid on an array, a wetted band on a blot, etc.

In practicing the subject methods, the first step (after any sample preparation step, as desired) is to contact the sample with a single nanopore. Typically, the nanopore is a component of a nanopore device in which the nanopore is present on a barrier which defines a cis side and trans side of the nanopore, such that sample can be contacted with the nanopore by placing the sample on one of the cis or trans sides of the nanopore. The side opposite the fluid sample is also in contact with a conductive fluid, where the fluid may be the same or different than the solvent of the fluid sample. In certain embodiments, the device is structured such that walls are provided to hold fluid on either the cis or trans sides of the nanopore, e.g. cis or trans fluid chambers or wells are present, where the chambers or wells are separated by the barrier/nanopore structure.

By nanopore is meant a structure having a channel or pore with a diameter of "nano" dimensions, where the inner diameter of the pore or channel typically ranges from about 1 to 10 nm, usually from at least about 2 to 4 to about 3 to 6 nm, where in many embodiments the diameter ranges from about 3 to 6 nm. The nanopore may be synthetic or naturally occurring, where naturally occurring nanopores include oligomeric protein channels, such as porins, and synthetic peptides and the like. Synthetic nanopores of interest include passageways bored through solid materials, such as found in the synthetic nanopore device described in greater detail infra.

As mentioned above, the nanopore devices are characterized in that the devices have a single nanopore present on a barrier. The barrier may be a rigid barrier or a flexible barrier, such as a thin film, e.g. a lipid bilayer. In one embodiment, the barrier into which the nanopore is inserted is a lipid bilayer fabricated from a wide variety of one or more different lipids, where suitable lipids include: phosphatidlycholine, phosphatidylserine, phosphatidylethanolamine, glycerol mono-oleate, and cholesterol. In yet other embodiments, the barrier is a thin sheet of a rigid crystalline material, e.g. mica, Formvar films, polycarbonate films or a similar low dielectric material, where the thickness of the sheet ranges from about 2 to 1000 nm, usually from about 5 to 100 nm. As mentioned above, the barrier/single nanopore structure has a cis and trans side that, during use of the device, separates the fluid sample from the another fluid, that may be the same or different than the solvent component of the fluid sample (i.e. the fluid sample less the nucleic acids).

In addition to the barrier/single nanopore structure, the nanopore devices finding use in the subject methods typically further include a means for applying an electric field to the fluid sample and across the nanopore in a manner such that nucleic acid molecules present in the fluid sample are sequentially translocated through the nanopore to the other side of the barrier, as described in greater detail infra. While any convenient means may be employed, the means for applying an electric field is generally two electrodes, one of which is present on the cis side of the barrier and the other of which is present on the trans side of the barrier.

A variety of suitable thin film support devices have been reported in the literature that may be used to support the nanopore/barrier used in the subject methods. Such devices include those described in: Brutyan et al., Biochimica et Biophysica Acta (1995) 1236:339–344; Wonderlin et al., Biophys. J. (1990) 58:289–297; Suarez-Isla et al. Biochemistry (1983) 22:2319–2323 as well as those disclosed and reviewed in U.S. patent application Ser. No. 08/405,735 entitled "Characterization of Individual Polymer Molecules Based on Monomer-Interface Interactions" filed on Mar. 17, 1995 and having a University of California reference number of 91-287-2; and the device described in copending U.S. patent application Ser. No. 60/107,307 filed Nov. 6, 1998, the disclosure of which is herein incorporated by reference.

A representative mica nanopore device that may be used in the subject methods is depicted in FIGS. 1A & 1B and described in detail in Example 1, infra. Briefly, figures A and B provide a diagram of a mica sheet being etched to product a nanopore. A thin mica sheet is cemented to a glass capillary tube and exposed to $^{252}$Cf fission products that on average product a single nuclear track through the mica. The tube is then filled with 1.0M KCl electrolyte and a silver—silver chloride electrode is inserted. A second plastic capillary tube filled with KCl and an electrode is placed above the mica as shown, and a mixture of 1.0 M KCl-20% hydrofluoric acid is added to fill the gap. A voltage of 100 mV is applied. Over a period of several minutes, the HF etches the track in the mica, producing a 6 nm diameter nanopore. When the pore is completely etched through the mica, an ionic current is measured and the mica is flushed to remove HF. The device is then ready for use in the subject methods.

Following contact of the fluid sample with the nanopore, e.g. the cis or trans side of the nanopore/barrier structure of the nanopore device, a least a portion of, if not all of, the nucleic acids present in the fluid sample are translocated through the nanopore, i.e. are moved from the cis to the trans side of the nanopore or vice versa. By "sequentially" is meant that only one nucleic acid present in the sample is moved through the nanopore at a time, since the nanopore is dimensioned so as to permit passage of only a single nucleic acid at any given time. By at least a portion is meant at least about 5, usually at least about 10 and more usually at least about 15 number % of the nucleic acids present in the sample. Translocation or movement of the nucleic acids in the sample through the nanopore is achieved using any convenient means, where generally movement is achieved by applying an electric field to the sample and across the nanopore. The applied electric field will be sufficiently strong to move the nucleic acids through the nanopore. The actual measured electric field that is applied across a typical nanopore 5 nm in length is generally from about 50 to 400 mV and usually 100 to 200 mV. When expressed as volts per cm, the electric field that is applied may range from about 50,000 to 500,000 volts per cm, where the applied electric field will typically range from about 100,000 to 400,000 volts per cm and more usually from about 150,000 to 300,000 volts per cm.

The period of time during which the electric field is applied to the fluid sample and across the nanopore varies depending on whether just a portion or substantially all of the nucleic acids present in the sample are to be translocated. Generally, the electric field is applied for at least about 1 ms, usually at least about 1 s and more usually at least about 10 s, where the electric field may be applied for 1 min or longer, but will generally not be applied for longer than about 10 min and usually will not be applied for longer than about 1 hour.

During the translocation step, the effect over time of the translocation on a measurable signal is determined. One convenient signal is the ion current through the pore. As such, in many embodiments, the ion current through the pore is measured during the translocation of the nucleic acids through the pore. In other words, the current through the pore is monitored during the translocation step. The measurements are generally of the amplitude of the current through the nanopore. In monitoring the nanopore during the translocation step, measurements of current through the pore are typically made at least every 1 s, usually at least every 0.1 s and more usually at least every 0.02 s.

In many embodiments, the measured data values, e.g. current amplitudes, are then manipulated to produce a current blockade profile or similar output capable of being compared against reference outputs such that the nature of the nucleic acid, i.e. the single or double strandedness of the nucleic acid passing through the pore can be determined. By current blockade profile is meant the collection of current blockade data points plotted versus a given period of time upon application of an applied electric field to a nanopore. The given period of time that a single nucleic acid molecule is examined is generally at least about 10 microseconds, usually at least about 100 microseconds and more usually at least about 250 microseconds and may be as long as 1 second or longer, but will usually not exceed about 5 milliseconds in length. The current blockade data points are derived from the observed change in ionic current through the nanopore from the cis to the trans side upon occupancy by the nucleic acid.

Following derivation of the collection of current blockade profiles during the translocation procedure, the derived current blockade profiles for a sample are then used to determine the presence or absence of double stranded or hybridized nucleic acids in the sample. By comparing the observed total current blockade profiles to reference current blockade profiles of single and double stranded nucleic acids, the presence of double stranded nucleic acids in a sample can readily be determined. In other words, one can look at the current blockade profiles to identify patterns that match the current blockade profile generated by translocation of a known double stranded nucleic acid through the nanopore. If patterns matching the control pattern are identified, then one knows that the sample includes double stranded or hybridized nucleic acids. The comparison can be done manually or automatically using computers and appropriate software.

The subject methods, in addition to being useful in determining the presence of single or double stranded nucleic acids in a sample, can also be used to determine the relative amounts of single and double stranded nucleic acids in a sample. In order to determine the relative amounts of single or double stranded nucleic acids in a sample, one can look qualitatively or quantitatively at the individual blockade profiles that are measured during translocation and derive a proportion of single to double stranded nucleic acids in the sample. The subject methods can also be used to quantitatively determine the numbers of single and double stranded nucleic acids in the sample, e.g. by counting the number of single stranded blockade profiles and the number of double stranded nucleic acid current blockade profiles observed during translocation. Again, these determinations may be done manually or using a computer means and appropriate software.

The subject methods find use in a variety of different applications where on wishes to determine the presence or absence of double stranded nucleic acids in a sample. For example, the subject methods find use in detecting hybridization events in assays where complementary nucleic acids are hybridized to each other and are detected. Examples of such hybridization assays include assays where one or more probes are combined with target nucleic acid and the occurrence of hybridization events in solution is detected. In such assays, unlabeled probe is contacted with the target nucleic acid sample. Next, the fluid sample is assayed according to the subject methods, and the presence of double-stranded nucleic acids in the sample is determined. The presence of double-stranded nucleic acids indicates that hybridization between the probe and target has occurred.

The following examples are offered by way of illustration and not be way of limitation.

EXPERIMENTAL

I. Preparation of Mica Nanopore Device

FIG. 1 provides a diagram of a mica sheet being etched to produce a nanopore. A thin mica sheet is cemented to a glass capillary tube and exposed to $^{252}$Cf fission products that, on average, produce a single nuclear track through the mica. The tube is then filled with 1.0 M KCl electrolyte and a silver—silver chloride electrode is inserted. A second plastic capillary tube filled with KCl and an electrode is placed above the mica as shown, and a mixture of 1.0 M KCl—20% hydrofluoric acid is added to fill the gap. A voltage of 100 mV is applied. Over a period of several minutes, the HF etches the track in the mica, producing a 6 nm diameter nanopore (See e.g. Bean et al., J. Appl. Phys. (1970) 41:1454–1459). When the pore is completely etched through the mica an ionic current is measured and the mica is flushed to remove HF.

II. Detection of Double Stranded DNA in a Sample

A 10 microliter aliquot of 10 micromolar single stranded 100 mer DNA probe molecules prepared on a DNA synthesizer in 1.0 M KCl is placed in two wells, each well having a 6 nm mica nanopore as prepared in Example I at the bottom and an electrical circuit so that a voltage of 100 mV can be applied through the pore. Under these conditions a 6 nm diameter nanopore will carry a current of approximately 1.0 nA. As the 100 mer probe molecules are driven through the nanopore by the voltage, they produce a series of current blockades, each lasting for a few hundred microseconds and reducing the current by 20% (to 0.8 nA) during the blockade. See FIG. 2A. Two unknown single stranded DNA fragments are then added to the wells, one with a complementary base sequence. A new series of higher magnitude blockades is observed in the well to which the complementary fragment was added. The higher amplitude blockades are absent in the well containing the non-complementary fragments. See FIG. 2B.

It is evident from the above results and discussion that novel methods of detecting the presence of duplex nucleic acid molecules, e.g. hybridized DNA molecules, are provided. As such, new methods of detecting the presence of hybridized probe/target complexes are provided in which a detectable label, such as a fluorescent or isotopic label, is not employed. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of detecting the presence of double stranded nucleic acid molecules in a sample that includes both double and single stranded nucleic acids said method comprising:
    (a) contacting said sample with a single nanopore:
    (b) translocating at least a portion of the nucleic acids present in said sample through said nanopore;
    (c) monitoring the current amplitude through said nanopore during said translocating; and
    (d) relating any changes in said current amplitude during said translocating to the presence or absence of double stranded nucleic acid molecules in said sample, wherein said relating comprises distinguishing signals produced by double stranded and single stranded nucleic acids;
    to detect the presence of double stranded nucleic acid molecules in said sample that includes both double and single stranded nucleic acids.

2. The method according to claim 1, wherein said double stranded nucleic acid molecule is DNA.

3. The method according to claim 1, wherein said sample is an aqueous sample.

4. The method according to claim 1, wherein substantially all of the nucleic acid molecules present in said sample are sequentially moved through said nanopore.

5. The method according to claim 1, wherein said nanopore is present in a barrier that separates a cis chamber from a trans chamber.

6. A method of determining the relative amounts of single and double stranded DNA molecules in a sample, said method comprising:
    (a) contacting said aqueous sample with a nanopore device comprising a barrier that includes a single nanopore;
    (b) translocating substantially all DNA molecules present in said sample through said nanopore by applying an electric field to said sample:
    (c) monitoring the current amplitude through said nanopore during said translocating and deriving a current blockade profile; and
    (d) relating said current blockade profile to the relative amounts of single and double stranded DNA molecules in said sample;
    to determine the relative amounts of single and double stranded DNA molecules in said sample.

7. The method according to claim 6, wherein said DNA molecules range in length from about 5 nt to 1000 nt.

8. The method according to claim 6, wherein said nanopore has a diameter ranging from about 3 nm to 6 nm.

9. The method according to claim 6, wherein said electric field has a strength ranges from about 50 mV to 400 my.

10. The method according to claim 6, wherein the quantitative amounts of single stranded and double stranded DNA molecules present in said sample are determined.

11. A method of quantitatively determining the amounts of single and double stranded DNA molecules in a sample, said method comprising:
    (a) contacting said aqueous sample with a nanopore device comprising a barrier that comprises a single nanopore;
    (b) translocating substantially all DNA molecules present In said sample through said nanopore by applying an electric field to said sample;
    (c) monitoring the current amplitude through said nanopore during said translocating to obtain a plurality of current amplitude measurements and deriving current blockade profiles from said plurality of current amplitude measurement; and
    (d) relating said current blockade profiles to the quantitative amounts of single and double stranded DNA molecules in said sample;
    to detect the quantitative amounts of single and double stranded DNA molecules in said sample
    whereby the quantitative amounts of single and double stranded DNA molecules in said sample are detected.

12. The method according to claim 11, wherein said DNA molecules range in length from about 5 nt to 1000 nt.

13. The method according to claim 11, wherein said nanopore has a diameter ranging in length from about 3 nm to 6 nm.

14. The method according to claim 11, wherein said electric field has a strength ranging from about 50 mV to 400 mV.

* * * * *